United States Patent [19]

Vescovini et al.

[11] Patent Number: 5,322,413

[45] Date of Patent: Jun. 21, 1994

[54] CENTRIFUGAL PUMP FOR LIQUIDS, IN PARTICULAR FOR BLOOD IN EXTRACORPOREAL CIRCULATION

[75] Inventors: Pietro Vescovini, Medolla; Nicola Ghelli, Casale; Ivo Panzani, Mirandola, all of Italy

[73] Assignee: Dideco S.p.A., Mirandola, Italy

[21] Appl. No.: 74,983

[22] Filed: Jun. 10, 1993

Related U.S. Application Data

[63] Continuation of Ser. No. 726,464, Jul. 8, 1991, abandoned.

[30] Foreign Application Priority Data

Jul. 16, 1990 [IT] Italy ................ 20949 A/90

[51] Int. Cl.⁵ ............................................. F01D 3/02
[52] U.S. Cl. ................................ 415/102; 415/206; 415/900; 417/420
[58] Field of Search ............ 415/10, 204, 205, 206, 415/219.1, 93, 97, 102, 900; 417/356, 420

[56] References Cited

U.S. PATENT DOCUMENTS

| | | | |
|---|---|---|---|
| 3,773,432 | 11/1973 | Chow et al. | 415/206 |
| 3,851,993 | 12/1974 | Foster | 415/203 |
| 3,864,055 | 2/1975 | Kletschka | 415/900 |
| 4,065,234 | 12/1977 | Yoshiyuki et al. | 417/420 |
| 4,080,112 | 3/1978 | Zimmermann | 417/420 |
| 4,507,048 | 3/1985 | Belenger et al. | |
| 4,514,139 | 4/1985 | Gurth | |
| 4,589,827 | 5/1986 | Clausen et al. | |
| 4,606,698 | 8/1986 | Clausen et al. | 415/900 |
| 4,625,712 | 2/1986 | Wampler | |
| 4,643,641 | 2/1987 | Clausen et al. | |
| 4,688,998 | 8/1987 | Olsen et al. | |
| 4,704,121 | 11/1987 | Moise | |
| 4,741,678 | 5/1988 | Nehring | |
| 4,779,614 | 10/1988 | Moise | |
| 4,840,535 | 6/1989 | Skarstad | |
| 4,898,518 | 2/1990 | Hubbard et al. | 415/900 |
| 4,908,012 | 3/1990 | Moise et al. | |
| 4,984,972 | 1/1991 | Clausen et al. | 415/900 |

FOREIGN PATENT DOCUMENTS

| | | | |
|---|---|---|---|
| 1063035 | 8/1959 | Fed. Rep. of Germany | |
| 1285244 | 8/1962 | France | 417/420 |
| 0237093 | 10/1987 | Japan | 417/420 |
| 356090 | 10/1961 | Switzerland | |
| 1108308 | 4/1968 | United Kingdom | |

*Primary Examiner*—Thomas E. Denion
*Attorney, Agent, or Firm*—Thomas Popovich & Associates

[57] ABSTRACT

In a centrifugal pump for liquids, in particular for blood in extracorporeal circulation, comprising a containment body for an impeller having the shape of a disk and comprising magnets inside it and having, on both faces, blades adapted for making contact with the liquid; the containment body has at least one liquid inflow connection, which is connected to ducts for conveying the liquid proximate to the center of the impeller on both sides thereof, and at least one liquid outflow connection; the containment body is shaped so that it can be removably inserted in a seat defined in a fixed base within which there is at least one magnet arranged so as to face the seat and being connected to means adapted for rotating it so as to rotationally entrain the impeller.

9 Claims, 6 Drawing Sheets

CENTRIFUGAL PUMP FOR LIQUIDS, IN PARTICULAR FOR BLOOD IN EXTRACORPOREAL CIRCULATION

This is a continuation of application Ser. No. 07/726,464 filed Jul. 8, 1991, now abandoned.

BACKGROUND OF THE INVENTION

1. Field of the Invention

The invention relates to centrifugal pump for liquids, in particular for blood in extracorporeal circulation.

2. Background of the Disclosure

It is known that in extracorporeal blood circuits shunted from a patient, particularly during certain operations, circulation is ensured by a pump which is inserted in the circuit, and the known art essentially provides two types of pump: peristaltic pumps and centrifugal pumps.

Centrifugal pumps essentially comprise a body for the containment of an impeller whereto a magnet is rigidly associated; said magnet is adapted for being rotated, thus rotationally entraining said impeller, by a second rotating magnet contained in a fixed base provided with a seat for the accommodation of said impeller containment body; said centrifugal pumps have considerable functional advantages with respect to peristaltic pumps, in particular as regards safety against high increases in pressure at the outlet end and as regards the possibility of sending air to the patient.

The constructive forms of centrifugal pumps present in the known art, however, are not devoid from disadvantageous characteristics, the first whereof is related to fluid mechanics: the presence of regions in which the blood is stagnant occurs in known pumps, with negative consequences from the point of view of the flow conveyed by the pump and from a strictly medical point of view.

A second disadvantageous characteristic in known centrifugal pumps is furthermore constituted by the presence of sealing gaskets which are adapted for preventing the access of blood to a chamber in which the magnet rigidly associated with the impeller is present; said sealing gaskets, which notoriously constitute a delicate element which is often the source of malfunctions, are arranged in a region in which the flow of liquid is not particularly active, and are therefore in bad functional conditions due to the overheating to which they are subjected.

In known centrifugal pumps, the sterilization operation also has problems, since it is necessary to resort to the adoption of sophisticated sealing gaskets in the method which uses a sterilization gas when one wishes to avoid resorting to the method which uses gamma rays, which compels a selection of special materials.

The aim of the present invention is, therefore, to provide a centrifugal pump for liquids, in particular for blood in extracorporeal circulation, having optimum characteristics from the fluid mechanics point of view and wherein all problems related to liquid tightness are eliminated. Within the scope of the above described aim, the invention is to provide a centrifugal pump suitable for any sterilization treatment without having to resort to particular contrivances.

SUMMARY OF THE INVENTION

The aim is achieved by a centrifugal pump for liquids, in particular for blood in extracorporeal circulation, according to the invention, comprises a body for the containment of an impeller, said impeller may have the shape of a disk with magnets inside it and is provided, on both faces, with blades adapted for making contact with the liquid; said containment body having at least one liquid inflow connection, connected to ducts for conveying said liquid proximate to the center of the impeller on both sides thereof, and having at least one liquid outflow connection. The containment body may be shaped so that it can be removably inserted into a seat defined in a fixed base within which there is at least one magnet, faces said seat and being connected to means adapted for rotating it, so as to rotationally entrain said impeller.

Further characteristics and advantages will become apparent from the description of two preferred, but not exclusive, embodiments of the invention, illustrated only by way of non-limitative example in the accompanying drawings.

DETAILED DESCRIPTION OF THE DRAWINGS

Figure 3:
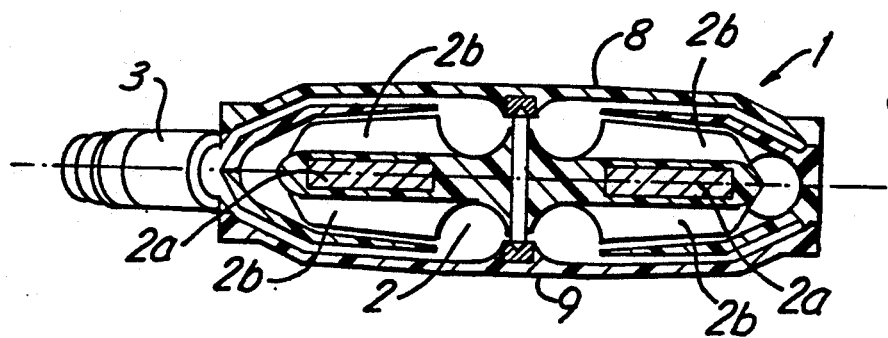
FIG. 3 is a sectional view taken along the plane III—III of FIG. 1.
Figure 2:
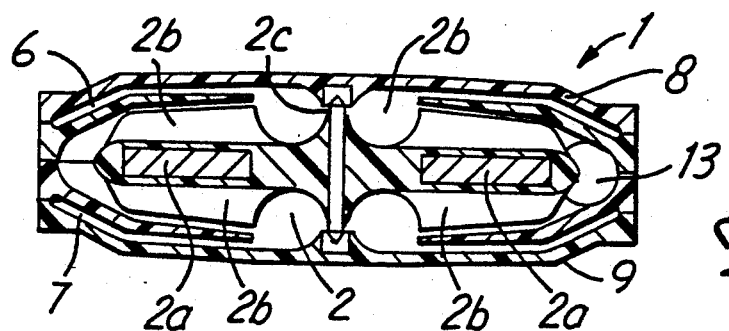
FIG. 2 is a sectional view taken along the plane II—II of FIG. 1.
Figure 1:
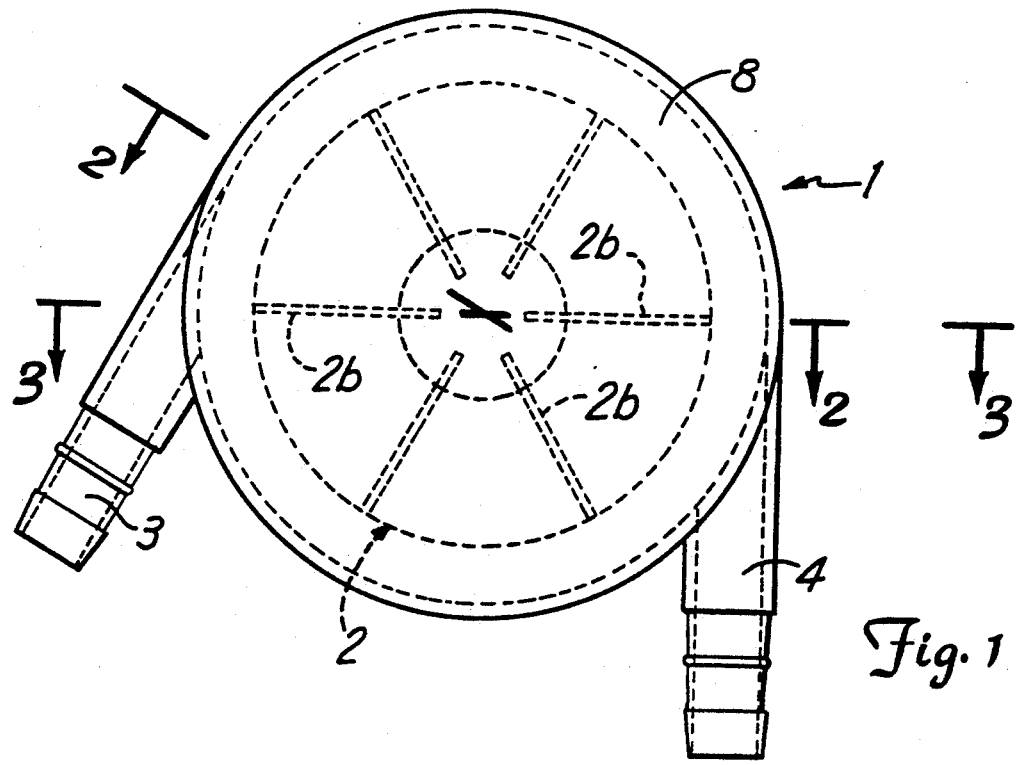
FIG. 1 is a view of the impeller containment body.

With reference to FIGS. 1 to 7, the reference numeral 1 generally indicates the containment body for the impeller 2, said body has a substantially cylindrical shape with substantially planar bases, a liquid inflow connection 3 and a liquid outflow connection 4 arranged substantially tangent to the lateral surface.

According to an important characteristic of the invention, the impeller 2 has the shape of a disk which comprises magnets 2a within itself and is provided, on both faces, with blades 2b intended to make contact with the liquid which is conveyed proximate to the center of said impeller 2 on both sides thereof by means of ducts connected to the inflow connection 3 and defined by virtue of the particular configuration of the body 1, which is now described in detail.

First, however, for completing the description of the impeller 2, it is to be noted that it has, at its axis of rotation, the pivot 2c which is monolithically associated therewith and is supported, at its ends, by the bushes 5a and 5b inserted within the body 1.

Returning to the detailed description of the body 1, which comprises the two cambered (curved baffels) elements 6 and 7, open at the center at 6a and 7a, having mating perimetric edges 6b and 7b and are rigidly associated for example by ultrasonic welding in the illustrated embodiment, which uses polycarbonate material; said elements 6 and 7 delimit a portion of space in which the impeller 2 is accommodated.

The body 1 furthermore comprises the covers 8 and 9 which are rigidly associated with the cambered elements 6 and 7 at the edge and are shaped so as to delimit, together with said elements, two lenticular portions (convex on both sides) of space 10 and 11 which are open toward the portion of space (at the center of the inside of the body) containing the impeller 2 at 6a and 7a and are suitable, as will shortly become apparent, for constituting ducts for the conveyance of the liquid to the impeller.

Figure 4:
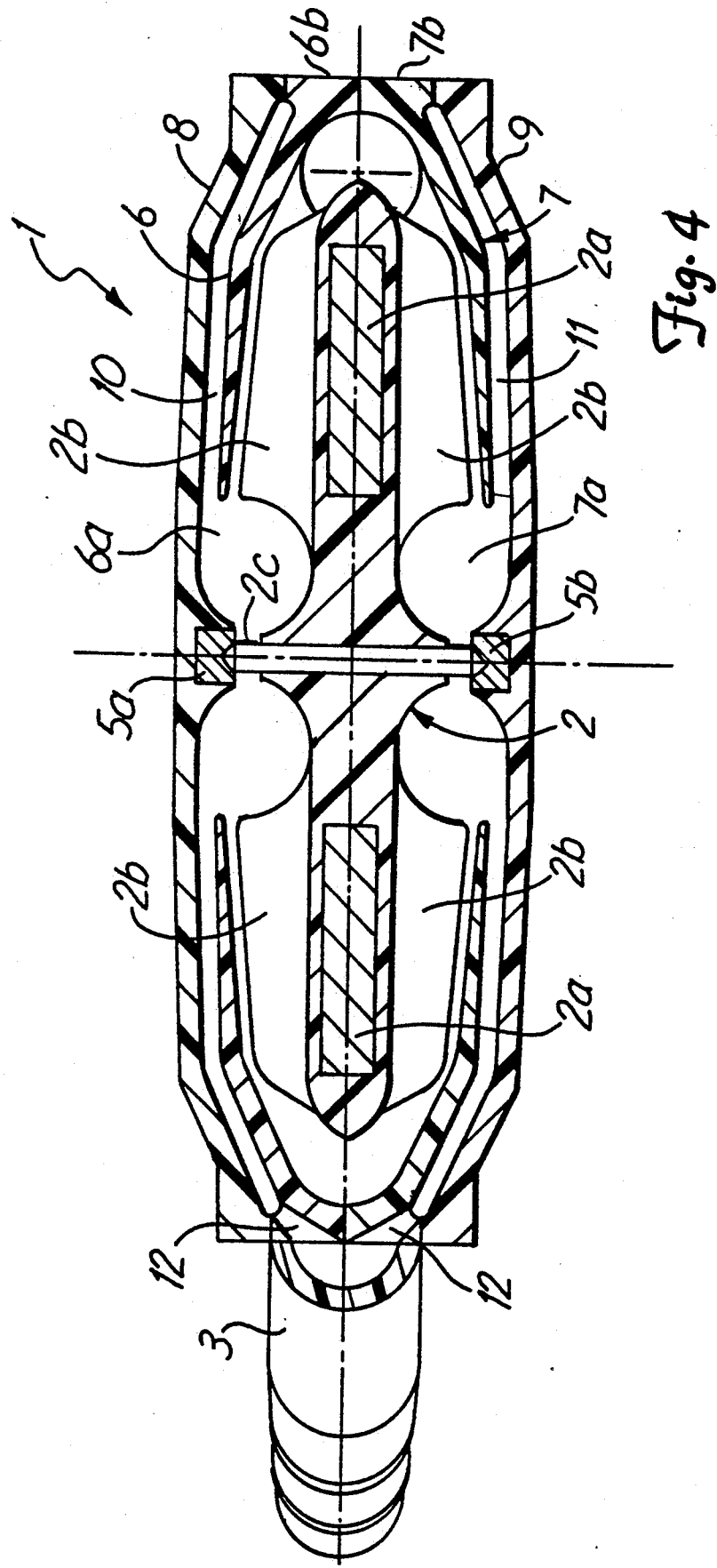
FIG. 4 is an enlarged-scale view of the cross-section shown in FIG. 3.
Figure 5:
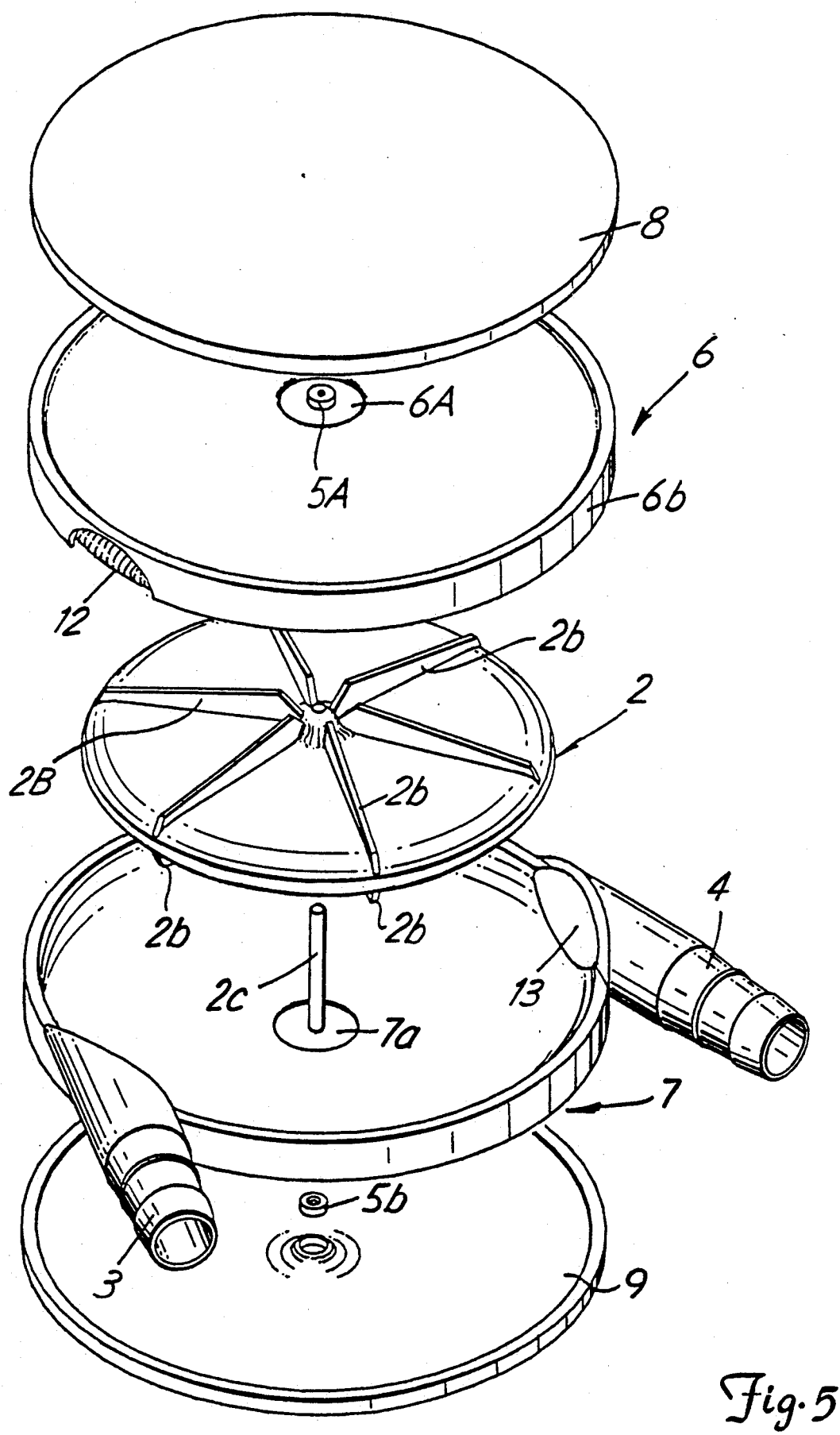
FIG. 5 is an exploded view of the elements which compose the pump.

The reference numeral 12 furthermore indicates a first opening defined at a portion of the mating edges 6b, 7b of the cambered elements 6 and 7 without interrupting, as is evident from FIG. 4, the continuity of the mating of said edges; said opening 12 is thus adapted for connecting the lenticular portions of space 10 and 11 to the inflow connection 2, arranged so as to face said opening 12.

The reference numeral 13 furthermore indicates a second opening also defined as a portion of the mating edges 6b, 7b but, unlike the first opening, interrupts the continuity of the mating between said edges, and thus the portion of space which accommodates the impeller 2 is connected to the outflow connection 4 arranged so as to face said opening 13.

Figure 6:
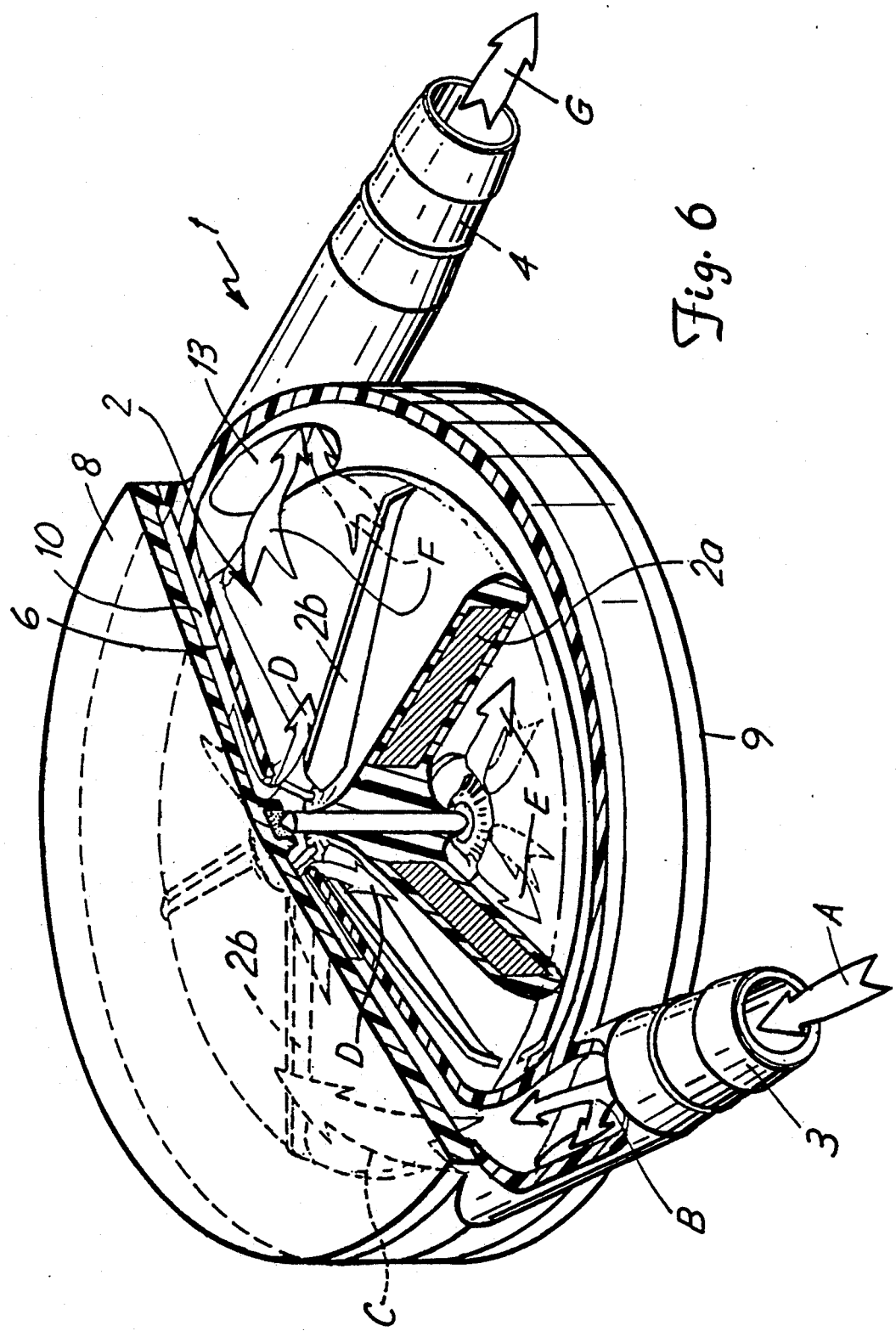
FIG. 6 is a view of the pump with an indication of the flow of the liquid inside it.

The circulation of the liquid produced inside the pump is clearly shown in FIG. 6. After entering from the connection 3 as indicated by the arrow A, the liquid flows through the first opening 12 where it is divided as indicated by the arrows labelled B and enters the lenticular portions of space 10 and 11 adjacent to the portion of space containing the impeller 2; the arrow C indicates the flow of liquid entering the lenticular portion of space 10. The entry of the portion of lenticular space 11 would be identical but cannot be seen in FIG. 6 as it is below the impeller 2.

Flowing through the lenticular portions of spaces 10 and 11, the liquid arrives above and below the impeller 2 at and passes through the openings 6a and 7a respectively, as indicated by the arrows D and E, respectively. The flow makes contact with the blades 2b of impeller 2 and then is driven by centrifugal force to enter, as indicated by the arrow F, the opening 13 leading to the outflow connection 4, wherefrom outflow occurs as indicated by the arrow G.

The described type of circulation is optimum to resist the formation of blood thrombin because there are no regions in which an even minimal stagnation of liquid occurs and also because the contacts of the pivot 2c of the impeller with the respective bushes 5a and 5b are included in an active flow of liquid which ensures their constant cooling and their operation in particularly advantageous conditions.

Figure 7:
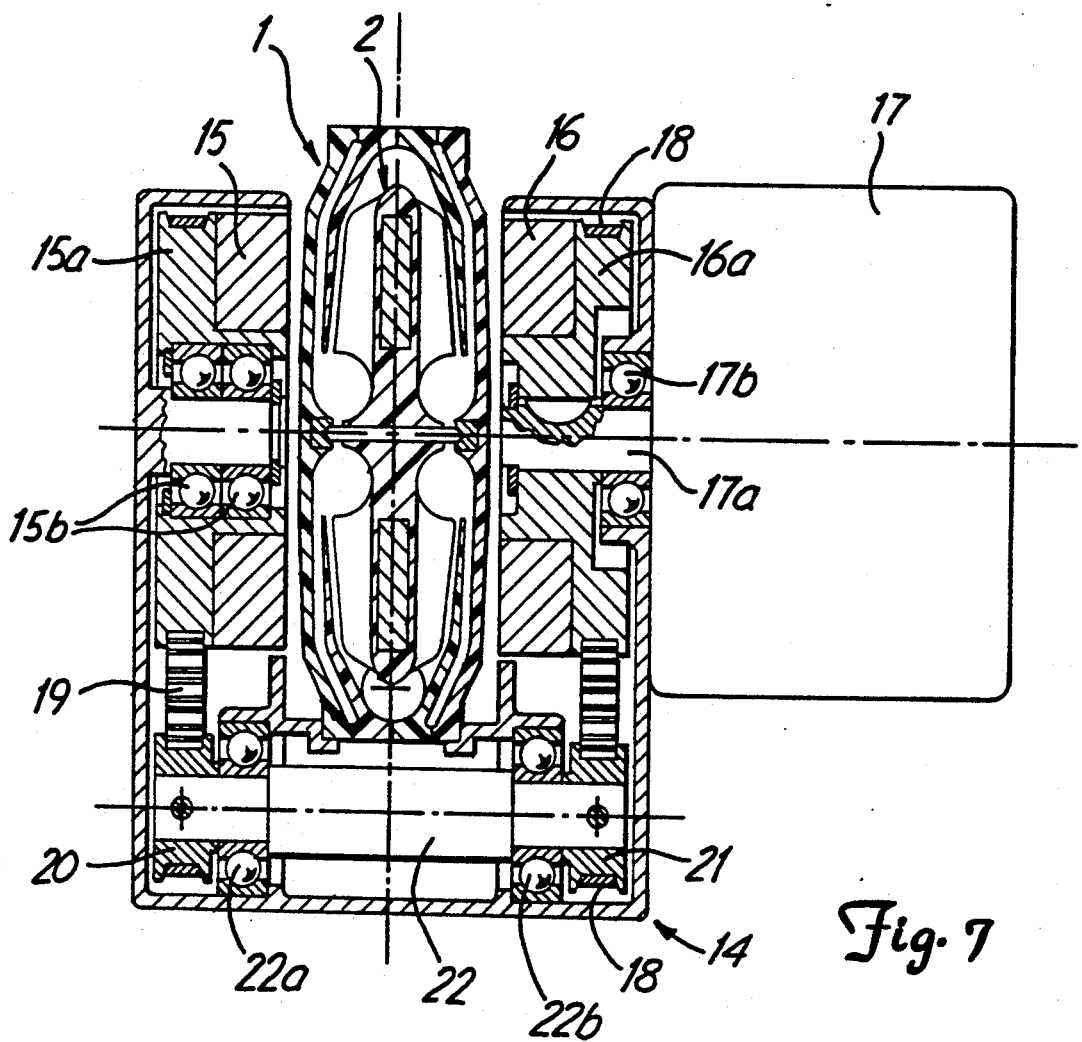
FIG. 7 is a sectional view of the pump inserted in the fixed base.

The body 1, according to what is illustrated in FIG. 7, is shaped so that it can be removably inserted in a seat defined in a fixed base 14 within which the two magnets 15 and 16 are present; said magnets are inserted in the magnet-holder disks 15a and 16a which rotate synchronously and are arranged so as to face on opposite sides the seat of the body 1 for the containment of the impeller 2 and are therefore such as to rotationally entrain said impeller in an axially balanced manner by acting on the magnets 2a comprised within said impeller.

The magnet-holder disk 16a is rotated by being keyed directly on the output shaft 17a of the motor 17 supported by the base 14 by means of the bearing 17b, and motion is transmitted synchronously from said disk to the magnet-holder disk 15a by means of a kinematic train which comprises toothed belts 18 and 19 operating in combination with the wheels 20 and 21 and keyed on the transmission shaft 22 supported by the bearings 22a and 22b.

The reference numeral 15b finally indicates the bearings supporting the magnet-holder disk 15a.

In the described embodiment of the invention there are no sealing gaskets, and therefore problems cannot arise from gasket failures or leaks. Operating conditions are also optimum in the embodiment shown in FIG. 8, which provides the presence of gaskets.

Figure 8:
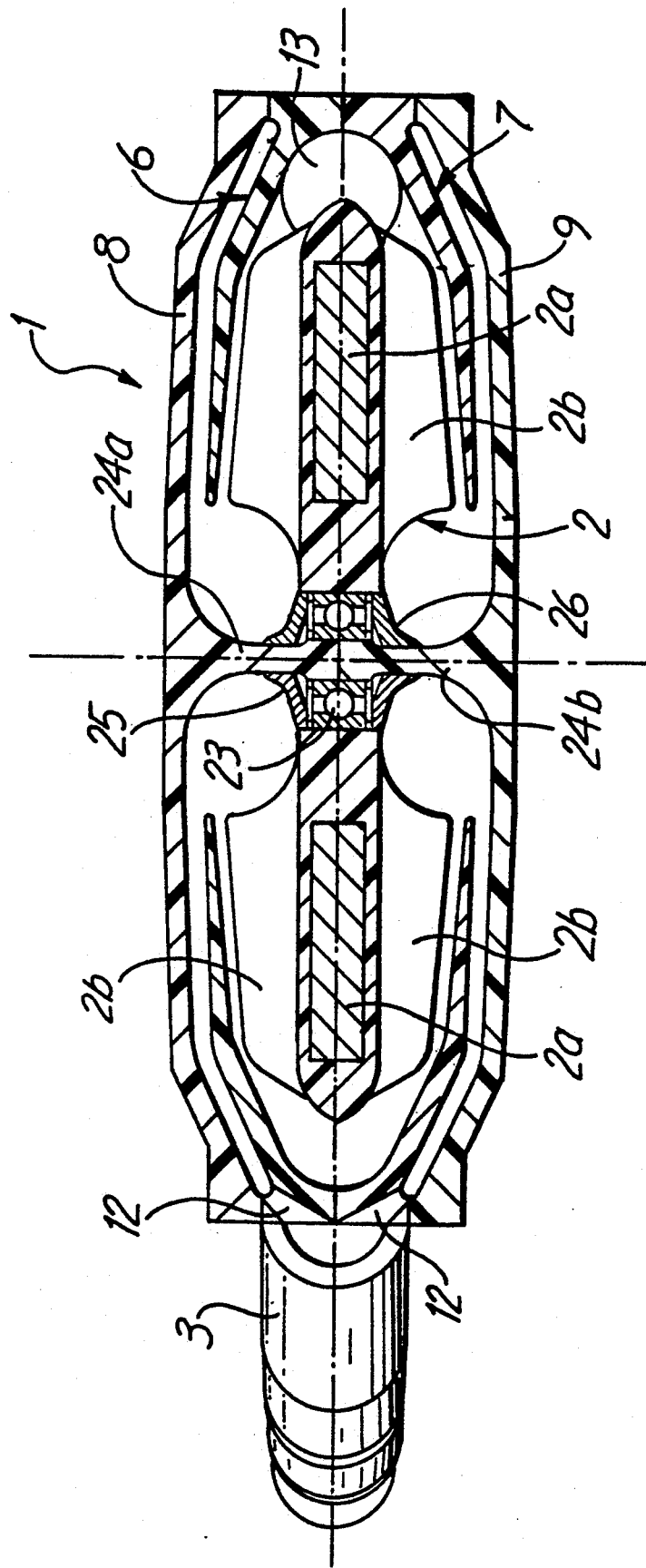
FIG. 8 is a sectional view of the pump according to a further embodiment.

In FIG. 8, there are containment body 1 and impeller 2 which has magnets 2a and blades 2b. In flow connection 3, cambered elements 6 and 7 function with the openings 12 and 13 and are a part of covers 8 and 9. In this embodiment, the impeller 2 rotates upon and about a rolling bearing 23 about a fixed axis, one half of which is formed by the tab 24a extending as part of cover 8, the other half being formed by the tab 24b extending as part of cover 9. Sealing gaskets 25 and 26 are arranged so as to protect the bearing 23. The sealing gaskets are in a region in which the flow of the liquid is active and therefore are, as previously mentioned, in the best locations to function and thereby prevent stagnated flow.

The described invention provides a pump with excellent fluid flow characteristics to eliminate seizure due to blood clotting and thrombin problems which occur in known pumps. It is important to note that the inside of the pump of this invention is easily accessible for sterilization by gas or by gamma rays. The pump operates simply.

The described invention is susceptible to numerous modifications and variations, all of which are within the scope of the inventive concept; all the details may furthermore be replaced with other technically equivalent elements.

In the practical execution of the invention, the materials employed, as well as the shapes and dimensions, may be varied according to the specific requirements.

What is claimed is:

1. A centrifugal pump for blood for the extracorporeal circulation thereof, comprising:
a body having an inner surface comprising a pump chamber;
an impeller located wholly within said pump chamber for pumping movement of the blood within the pump chamber, the impeller rotatable about an impeller center and having a disk shape with a pair of opposed sides defining major impeller surfaces each having an impeller surface center, the impeller having magnets located between the pair of opposed sides for driving the impeller around the impeller center by rotating magnet means located outside the pump chamber, the impeller fixedly attached to first impeller guide means, said body further comprising second impeller guide means, said first and second impeller guide means rotatably connected to each other for the rotation of the impeller around the impeller center;
a plurality of blades on the impeller and extending from the major impeller surfaces in opposite direction, the blades set to make contact with the blood for directing the passage of the blood radially outwardly along the impeller for the pumping movement;
inflow connection means on the body for receiving blood;

outflow connection means on the body for receiving blood; and baffle means within the pump chamber located for directing the flow of the blood from the inflow connection means, toward the impeller surface centers of the opposed sides of the impeller, and radially outwardly from each impeller surface center toward the outflow connection means.

2. The centrifugal pump of claim 1 wherein said first impeller guide means comprises a shaft having opposite ends, and said second impeller guide means comprises opposed bushings inserted in the inner surface of the body.

3. The centrifugal pump of claim 1 wherein said first impeller guide means comprises a bearing located at the impeller center, and the second impeller guide means comprises a pivot shaft having opposite ends fixed and rigidly associated within the inner surface of the body.

4. The centrifugal pump of claim 1 further comprising a nonmovable base having seating means shaped to removably receive and hold the body, and
wherein rotating magnet means are located in the seating means, and the rotating magnet means face the body to rotationally drive the impeller by virtue of the magnetic force between the rotating magnet means and the magnets located in the impeller.

5. The centrifugal pump of claim 3 wherein the impeller bearing includes rollers protected from contact with blood flow through the pump chamber by a pair of sealing gaskets positioned near each impeller surface center.

6. The centrifugal pump of claim 1 wherein the body has opposed covers each of substantially cylindrical and generally planar shape and a lateral surface thereabout and wherein the inflow and outflow connections means are arranged substantially tangent to the lateral surface.

7. The centrifugal pump of claim 6 wherein lenticular spaces are formed between the baffle means and the covers, the lenticular spaces are in fluid communication with each of the impeller surface centers, the lenticular spaces connected to the inflow connection means to allow flow of blood toward the impeller surface centers, and the impeller surface centers are in fluid communication with the outflow connection means.

8. The centrifugal pump of claim 1 wherein the body has two covers, a peripheral edge and said baffle means comprising a cambered element associated with each cover and extending radially inwardly from said peripheral edge and open at the center to define a lenticular chamber portion between one side of each cambered element and its associated cover and an impeller chamber portion between the other side of each cambered element and the impeller, each cover and said baffle means having rigid edges about their periphery with the rigid edges of the covers and the baffle means shaped to mate with each other along mating edges, the cambered elements shaped for minimizing the space available within the pump chamber to accommodate the impeller;
a first opening located at a portion of the mating edges and shaped to not interrupt the continuity of the mating edges, the first opening connecting the lenticular chamber portions to the inflow connection means; and
a second opening at another portion of the mating edges and shaped so as not to interrupt the continuity of the mating edges, the second opening connecting the impeller chamber portion to the outflow connection means.

9. The centrifugal pump of claim 4 wherein the rotating magnet means comprises two magnets held within magnet-holder disks operatively connected for ensuring synchronous motion of the magnets.

* * * * *